(12) United States Patent
Addison et al.

(10) Patent No.: US 10,499,835 B2
(45) Date of Patent: Dec. 10, 2019

(54) METHODS AND SYSTEMS FOR DETERMINING FLUID RESPONSIVENESS IN THE PRESENCE OF NOISE

(71) Applicant: Covidien LP, Mansfield, MA (US)

(72) Inventors: Paul S. Addison, Edinburgh (GB); Scott McGonigle, Edinburgh (GB); James N. Watson, Dunfermline (GB)

(73) Assignee: Covidien LP, Mansfield, MA (US)

( * ) Notice: Subject to any disclaimer, the term of this patent is extended or adjusted under 35 U.S.C. 154(b) by 947 days.

(21) Appl. No.: 15/064,500

(22) Filed: Mar. 8, 2016

(65) Prior Publication Data

US 2016/0278673 A1     Sep. 29, 2016

Related U.S. Application Data

(60) Provisional application No. 62/137,671, filed on Mar. 24, 2015.

(51) Int. Cl.
*A61B 5/1455* (2006.01)
*A61B 5/00* (2006.01)
(Continued)

(52) U.S. Cl.
CPC ...... *A61B 5/14551* (2013.01); *A61B 5/02416* (2013.01); *A61B 5/7207* (2013.01); (Continued)

(58) Field of Classification Search
CPC ............ A61B 5/14551; A61B 5/02416; A61B 5/7207; A61B 5/7275; G06F 19/00
See application file for complete search history.

(56) References Cited

U.S. PATENT DOCUMENTS 4,781,195 A    11/1988  Martin
4,846,183 A    7/1989   Martin
(Continued)

FOREIGN PATENT DOCUMENTS

WO   WO 1998/51212   11/1998
WO   WO 2011/041090   4/2011
WO   WO 2014/166504  10/2014

OTHER PUBLICATIONS

Addison et al., Developing an algorithm for pulse oximetry derived respiratory rate (RRoxi), Journal of Clinical Monitoring and Computing, Jan. 10, 2012, vol. 26: pp. 45-51. (Year: 2012).*
(Continued)

*Primary Examiner* — Eric F Winakur
*Assistant Examiner* — Marjan Fardanesh
(74) *Attorney, Agent, or Firm* — Shumaker & Sieffert, P.A.

(57) ABSTRACT

Methods and systems are provided for determining fluid responsiveness in the presence of noise. The system may determine an instantaneous value indicative of fluid responsiveness. In some embodiments, the system may determine a difference between an instantaneous value indicative of fluid responsiveness and a previous value indicative of fluid responsiveness, and select an update characteristic based on whether the difference indicates that the fluid responsiveness is increasing or decreasing. In some embodiments, the system may determine a parameter indicative of fluid responsiveness based on the update characteristic and a previously reported value indicative of fluid responsiveness.

21 Claims, 7 Drawing Sheets

(51) Int. Cl.
*A61B 5/024* (2006.01)
*G16H 50/30* (2018.01)
*G16H 20/40* (2018.01)

(52) U.S. Cl.
CPC ........... *A61B 5/7275* (2013.01); *G16H 20/40* (2018.01); *G16H 50/30* (2018.01)

(56) References Cited

U.S. PATENT DOCUMENTS

| | | | |
|---|---|---|---|
| 4,942,877 | A | 7/1990 | Sakai et al. |
| 5,152,296 | A | 10/1992 | Simons |
| 5,253,646 | A | 10/1993 | Delpy et al. |
| 5,267,562 | A | 12/1993 | Ukawa et al. |
| 5,273,036 | A | 12/1993 | Kronberg et al. |
| 5,343,818 | A | 9/1994 | McCarthy et al. |
| 5,355,882 | A | 10/1994 | Ukawa et al. |
| 5,564,417 | A | 10/1996 | Chance |
| 6,064,898 | A | 5/2000 | Aldrich |
| 6,129,675 | A | 10/2000 | Jay |
| 6,361,501 | B1 | 3/2002 | Amano et al. |
| 6,434,408 | B1 | 8/2002 | Heckel |
| 6,553,242 | B1 | 4/2003 | Sarussi |
| 6,594,513 | B1 | 7/2003 | Jobsis et al. |
| 6,615,064 | B1 | 9/2003 | Aldrich |
| 6,701,170 | B2 | 3/2004 | Stetson |
| 6,702,752 | B2 | 3/2004 | Dekker |
| 6,709,402 | B2 | 3/2004 | Dekker |
| 6,773,397 | B2 | 8/2004 | Kelly |
| 6,801,798 | B2 | 10/2004 | Geddes et al. |
| 6,829,496 | B2 | 12/2004 | Nagai et al. |
| 6,839,582 | B2 | 1/2005 | Heckel |
| 6,839,659 | B2 | 1/2005 | Tarassenko et al. |
| 7,044,917 | B2 | 5/2006 | Arnold |
| 7,422,562 | B2 * | 9/2008 | Hatib ................... A61B 5/02 600/485 |
| 7,976,472 | B2 | 7/2011 | Kiani |
| 8,221,319 | B2 | 7/2012 | Lovejoy |
| 8,251,912 | B2 | 8/2012 | Shelley et al. |
| 8,298,151 | B2 | 10/2012 | Riobo Aboy et al. |
| 8,414,499 | B2 | 4/2013 | Al-Ali et al. |
| 8,529,458 | B2 | 9/2013 | Kim et al. |
| 8,532,754 | B2 | 9/2013 | Cannesson |
| 8,551,005 | B2 | 10/2013 | Baruch |
| 2003/0236647 | A1 | 12/2003 | Yoon et al. |
| 2004/0059210 | A1 | 3/2004 | Stetson |
| 2004/0122300 | A1 | 6/2004 | Boas et al. |
| 2004/0186358 | A1 | 9/2004 | Chernow et al. |
| 2008/0188760 | A1 * | 8/2008 | Al-Ali ................ A61B 5/14551 600/507 |
| 2009/0048527 | A1 | 2/2009 | Hatib et al. |
| 2009/0326353 | A1 | 12/2009 | Watson et al. |
| 2010/0324827 | A1 | 12/2010 | Addison et al. |
| 2011/0077532 | A1 * | 3/2011 | Kim ..................... A61B 5/0205 600/485 |
| 2011/0270097 | A1 * | 11/2011 | Aboy ................. A61B 5/02116 600/484 |
| 2011/0276275 | A1 * | 11/2011 | Addison ........... A61B 5/14551 702/19 |
| 2012/0053433 | A1 | 3/2012 | Chamoun et al. |
| 2012/0296219 | A1 | 11/2012 | Chon et al. |
| 2014/0058229 | A1 | 2/2014 | Su et al. |
| 2014/0073862 | A1 * | 3/2014 | Rodriguez-Llorente .................... A61B 5/7203 600/301 |
| 2014/0073889 | A1 | 3/2014 | Su et al. |
| 2014/0316278 | A1 | 10/2014 | Addison et al. |

OTHER PUBLICATIONS

Smith, "Scientist and Engineer's guide to Digital Signal Processing", Ch15 Moving Average Filters, pp. 277-284, 2011 (Year: 2011).*

Smith, "Scientist and Engineer's guide to Digital Signal Processing", Ch19 Recursive Filters, pp. 319-332, 2011 (Year: 2011).*

Challoner, A.V.J., Photoelectric Plethysmography for Estimating Cutaneous Blood Flow, in "Non-Invasive Physiological Measurements," Rolfe, P., Academic Press Inc., London, 1979, pp. 125-151.

Dorlas, J.C. and Nijboer, J.A., "Photo-Electric Plethysmography as a Monitoring Device in Anesthesia. Application and Interpretation," British Journal of Anesthesia, 1985; 57(5), pp. 524-530.

Michard, Frederic, et al., "Clinical use of Respiratory Changes in Arterial Pulse Pressure to Monitor the Hemodynamic Effects of PEEP," Am J Respir Crit Care Med, Mar. 1999; 159(3), pp. 935-939.

Partridge, Brian L., "Use of Pulse Oximetry as a Noninvasive Indicator of Intravascular Volume Status," Journal of Clinical Monitoring, Oct. 1987; 3(4), pp. 263-268.

Shamir, M., et al., "Pulse Oximetry Plethysmographic Waveform During Changes in Blood Volume," British Journal of Anesthesia, 1999; 82(2), pp. 178-181.

* cited by examiner

METHODS AND SYSTEMS FOR DETERMINING FLUID RESPONSIVENESS IN THE PRESENCE OF NOISE

CROSS REFERENCE TO RELATED APPLICATION

This application claims the benefit of U.S. Provisional Application No. 62/137,671, filed Mar. 24, 2015, which is hereby incorporated by reference herein in its entirety.

SUMMARY

The present disclosure relates to determining fluid responsiveness, and more particularly, towards determining fluid responsiveness with a response time that is based on whether fluid responsiveness is increasing or decreasing.

The present disclosure provides embodiments for a physiological monitoring system comprising a light detecting sensor and a processor. The light detecting sensor is configured to detect light absorbed through tissue of a subject, and generate a physiological signal based on the detected light. The processor is coupled to the sensor and configured to receive the physiological signal. The processor is further configured to determine an instantaneous value indicative of fluid responsiveness of the subject based on the physiological signal and determine a difference between the instantaneous value indicative of fluid responsiveness and a previous value indicative of fluid responsiveness of the subject. The processor is further configured to select an update characteristic based on whether the difference indicates the fluid responsiveness of the subject is increasing or decreasing. The processor is further configured to determine a parameter indicative of fluid responsiveness of the subject based on the selected update characteristic and a previously reported value indicative of fluid responsiveness.

The present disclosure provides embodiments for a method of determining fluid responsiveness of a subject. The method comprises receiving a physiological signal indicative of light attenuated by the subject. The method further comprises determining, using a processor, an instantaneous value indicative of fluid responsiveness of the subject based on the physiological signal. The method further comprises determining, using the processor, a difference between the instantaneous value indicative of fluid responsiveness and a previous value indicative of fluid responsiveness of the subject. The method further comprises selecting, using the processor, an update characteristic based on whether the difference indicates the fluid responsiveness of the subject is increasing or decreasing. The method further comprises determining, using the processor, a parameter indicative of fluid responsiveness of the subject based on the selected update characteristic and a previously reported value indicative of fluid responsiveness.

The present disclosure provides embodiments for a physiological monitoring system comprising an input, a fluid responsiveness calculator and a fluid responsiveness differential calculator. The input is configured to receive a physiological signal, wherein the physiological signal is indicative of light absorbed by a subject. The fluid responsiveness calculator is coupled to the input and configured to determine an instantaneous value indicative of fluid responsiveness of the subject based on the physiological signal. The fluid responsiveness differential calculator is coupled to the fluid responsiveness calculator and configured to determine a difference between the instantaneous value indicative of fluid responsiveness and a previous value indicative of fluid responsiveness of the subject. The fluid responsiveness calculator is further configured to select a filter weight for the instantaneous value indicative of fluid responsiveness based on whether the difference indicates the fluid responsiveness of the subject is increasing or decreasing, wherein the selected filter weight is smaller when the difference indicates the fluid responsiveness of the subject is increasing. The fluid responsiveness calculator is further configured to determine a parameter indicative of fluid responsiveness of the subject based on the selected filter weight, the instantaneous value indicative of fluid responsiveness, and one or more previous values indicative of fluid responsiveness.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
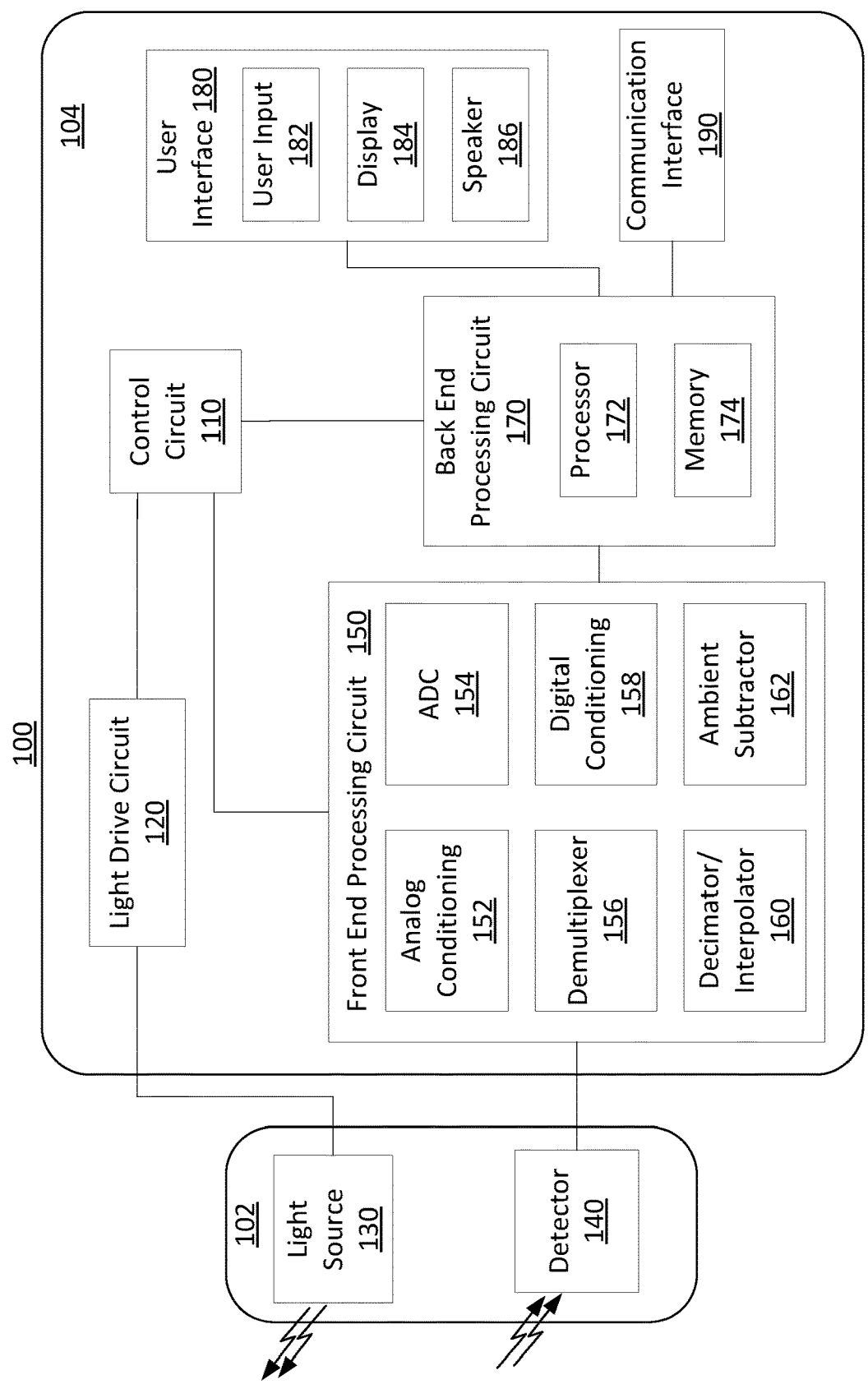
FIG. 1 shows a block diagram of an illustrative physiological monitoring system in accordance with some embodiments of the present disclosure.

The present disclosure is directed towards determining fluid responsiveness for a subject, and more particularly, towards determining fluid responsiveness with a response time that is based on whether fluid responsiveness is increasing or decreasing. In one embodiment, a monitor is configured to determine a difference between an instantaneous fluid responsiveness value and a previous fluid responsiveness value, select an update characteristic based on whether the difference indicates fluid responsiveness is increasing or decreasing, and determine fluid responsiveness based on the selected update characteristic and one or more previous values indicative of fluid responsiveness.

Fluid is commonly delivered to a patient in order to improve the patient's hemodynamic status. Fluid is delivered with the expectation that it will increase the patient's cardiac preload, right ventricular end-diastolic volume, left ventricular end-diastolic volume, stroke volume, and cardiac output, resulting in improved oxygen delivery to the organs and tissue. Fluid delivery may also be referred to as volume expansion, fluid therapy, fluid challenge, or fluid loading.

However, improved hemodynamic status is not always achieved by fluid loading. Moreover, inappropriate fluid loading may worsen a patient's status, such as by causing hypovolemia to persist (potentially leading to inadequate organ perfusion), or by causing hypervolemia (potentially leading to peripheral or pulmonary edema).

Respiratory variation in the arterial blood pressure waveform is known to be a good predictor of a patient's response to fluid loading, or fluid responsiveness. Fluid responsiveness represents a prediction of whether such fluid loading will improve blood flow within the patient. Fluid responsiveness refers to the response of stroke volume or cardiac output to fluid administration. A patient is said to be fluid responsive if fluid loading does accomplish improved blood flow, such as by an improvement in cardiac output or stroke volume index by about 15% or more. In particular, the pulse pressure variation (PPV) parameter from the arterial blood pressure waveform has been shown to be a good predictor of fluid responsiveness. This parameter can be monitored while adding fluid incrementally, until the PPV value indicates that the patient's fluid responsiveness has decreased, and more fluid will not be beneficial to the patient. This treatment can be accomplished without needing to calculate blood volume or cardiac output directly. This approach, providing incremental therapy until a desired target or endpoint is reached, may be referred to as goal-directed therapy (GDT).

However, determining the PPV is an invasive procedure, requiring the placement of an arterial line in order to obtain the arterial blood pressure waveform. This invasive procedure is time-consuming and presents a risk of infection to the patient. Respiratory variation in a photoplethysmograph (PPG) signal may provide a non-invasive alternative to PPV. The PPG signal can be obtained non-invasively, such as from a pulse oximeter. One measure of respiratory variation in the PPG is the Delta POP metric, which is a measure of the strength of respiratory-induced amplitude modulations of the PPG. This metric assesses changes in the pulse oximetry plethysmograph, and is abbreviated as ΔPOP or DPOP. In some embodiments, DPOP is determined instantaneously over a first window, which may be a fixed period or may be a period corresponding to a breath of the subject, and the DPOP value used for diagnosis is an average of the instantaneous DPOP values determined for multiple windows. Thus, it is desirable to ensure that the instantaneous DPOP values used in averaging are of good quality.

While there is a favorable correlation between DPOP and PPV, PPG signals used to determine the instantaneous DPOP values are still susceptible to noise. When such noise enters the PPG signal, it may cause one or more of the cardiac pulses to change its morphology, which may lead to using erroneous amplitudes when calculating DPOP. The erroneous amplitudes may in turn lead to a significant change in instantaneous DPOP values even when the subject's actual fluid responsiveness is generally stable. Such noise may particularly affect maximum amplitudes used to calculate the instantaneous DPOP values and in turn cause a significant erroneous increase in instantaneous DPOP values as compared to previous DPOP values. In accordance with the present disclosure, DPOP is determined with a response time that is based on whether DPOP is increasing or decreasing. In some embodiments, an update characteristic may be selected based on whether the instantaneous DPOP values are increasing or decreasing, and the DPOP value used for diagnosis may be determined based on the update characteristic and a previously reported DPOP value. For example, the update characteristic may be a weight given to the instantaneous DPOP value, wherein less weight is given to an instantaneous DPOP value when the DPOP values are increasing than when the DPOP values are decreasing or remaining stable. As another example, the update characteristic may be an amount of change to be added to a previously reported DPOP value, wherein the magnitude the amount of change may be greater when the instantaneous DPOP values are decreasing or stable than when the instantaneous DPOP values are increasing.

The foregoing techniques may be implemented in an oximeter. An oximeter is a medical device that may determine the oxygen saturation of an analyzed tissue. One common type of oximeter is a pulse oximeter, which may non-invasively measure the oxygen saturation of a patient's blood (as opposed to measuring oxygen saturation invasively by analyzing a blood sample taken from the patient). Oximeters may be included in patient monitoring systems that measure and display various blood characteristics including, for example, blood oxygen saturation (e.g., arterial, venous, regional, or a combination thereof). Such patient monitoring systems, in accordance with the present disclosure, may also measure and display additional or alternative physiological parameters such as pulse rate, respiration rate, respiration effort, blood pressure, hemoglobin concentration (e.g., oxygenated, deoxygenated, and/or total), cardiac output, fluid responsiveness parameters, any other suitable physiological parameters, or any combination thereof.

An oximeter may include a light sensor that is placed at a site on a subject. For example, the light sensor may be placed on a fingertip, toe, forehead or earlobe, or in the case of a neonate, across a foot or hand. The light sensor may also be placed at any other suitable location on a subject. The oximeter may use a light source to pass light through blood perfused tissue and photoelectrically sense the absorption of the light in the tissue. The oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, an inverted signal, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters.

In some embodiments, the photonic signal interacting with the tissue is of one or more wavelengths that are attenuated by the blood in an amount representative of the blood constituent concentration. Red and infrared (IR) wavelengths may be used because it has been observed that highly oxygenated blood will absorb relatively less red light and more IR light than blood with a lower oxygen saturation. By comparing the intensities of two wavelengths at different points in the pulse cycle, it is possible to estimate the blood oxygen saturation of hemoglobin in arterial blood.

The system may process data to determine physiological parameters using techniques well known in the art. For example, the system may determine arterial blood oxygen saturation using two wavelengths of light and a ratio-of-ratios calculation. As another example, the system may determine regional blood oxygen saturation using two wavelengths of light and two detectors located at different distances from the emitters. The system also may identify pulses and determine pulse amplitude, respiration, respiratory variation, fluid responsiveness, blood pressure, other suitable parameters, or any combination thereof, using any suitable calculation techniques. In some embodiments, the system may use information from external sources (e.g., tabulated data, secondary sensor devices) to determine physiological parameters.

It will be understood that the techniques described herein are not limited to oximeters and may be applied to any suitable physiological monitoring device.

FIG. 1 shows a block diagram of illustrative physiological monitoring system 100 in accordance with some embodiments of the present disclosure. System 100 may include a sensor 102 and a monitor 104 for generating and processing sensor signals that include physiological information of a subject. In some embodiments, sensor 102 and monitor 104 may be part of an oximeter. In some embodiments, system 100 may include more than one sensor 102.

Sensor 102 of physiological monitoring system 100 may include light source 130 and detector 140. Light source 130 may be configured to emit photonic signals having one or more wavelengths of light (e.g. red and IR) into a subject's tissue. For example, light source 130 may include a red light emitting light source and an IR light emitting light source, e.g. red and IR light emitting diodes (LEDs), for emitting light into the tissue of a subject to generate sensor signals that include physiological information. In one embodiment, the red wavelength may be between about 600 nm and about 750 nm, and the IR wavelength may be between about 800 nm and about 1000 nm. It will be understood that light source 130 may include any number of light sources with any suitable characteristics. In embodiments where an array of sensors is used in place of single sensor 102, each sensor may be configured to emit a single wavelength. For example, a first sensor may emit only a red light while a second may emit only an IR light.

It will be understood that, as used herein, the term "light" may refer to energy produced by radiative sources such as electromagnetic radiative sources and may include, for example, any wavelength within the radio, microwave, millimeter wave, infrared, visible, ultraviolet, gamma ray or X-ray spectra. Detector 140 may be chosen to be specifically sensitive to the chosen targeted energy spectrum of light source 130.

In some embodiments, detector 140 may be configured to detect the intensity of light at the red and IR wavelengths. In some embodiments, an array of sensors may be used and each sensor in the array may be configured to detect an intensity of a single wavelength. In operation, light may enter detector 140 after passing through the subject's tissue. Detector 140 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detector 140. After converting the received light to an electrical signal, detector 140 may send the detection signal to monitor 104, where the detection signal may be processed and physiological parameters may be determined. In some embodiments, the detection signal may be preprocessed by sensor 102 before being transmitted to monitor 104. Although only one detector 140 is depicted in FIG. 1, in some embodiments, sensor 102 may include additional detectors located at different distances from the light source 130.

Sensor 102 may also include additional components not depicted in FIG. 1. For example, sensor 102 may include an internal power source (e.g., a battery) and a wireless transmitter for communicating with monitor 104. As another example, sensor 102 may include additional sensor components such as, for example, a temperature sensor.

In the embodiment shown, monitor 104 includes control circuit 110, light drive circuit 120, front end processing circuit 150, back end processing circuit 170, user interface 180, and communication interface 190. Monitor 104 may be communicatively coupled to sensor 102 via wired communication, wireless communication, or both. Wired communication may use a cable that includes one or more electronic conductors, one or more optical fibers, any other suitable communication components, any suitable insulation or sheathing, or any combination thereof. Monitor 104 may include a sensor port for mating with the cable.

Control circuit 110 may be coupled to light drive circuit 120, front end processing circuit 150, and back end processing circuit 170, and may be configured to control the operation of these components. In some embodiments, control circuit 110 may be configured to provide timing control signals to coordinate their operation. For example, light drive circuit 120 may generate a light drive signal, which may be used to turn on and off light source 130, based on the timing control signals. The front end processing circuit 150 may use the timing control signals to operate synchronously with light drive circuit 120. For example, front end processing circuit 150 may synchronize the operation of an analog-to-digital converter and a demultiplexer with the light drive signal based on the timing control signals. In addition, the back end processing circuit 170 may use the timing control signals to coordinate its operation with front end processing circuit 150.

Light drive circuit 120, as discussed above, may be configured to generate a light drive signal that is provided to light source 130 of sensor 102. The light drive signal may, for example, control the intensity of light source 130 and the timing of when light source 130 is turned on and off. In some embodiments, light drive circuit 120 may comprise a power supply and a switch for selectively applying power to light source 130. When light source 130 is configured to emit two or more wavelengths of light, the light drive signal may be configured to control the operation of each wavelength of light. The light drive signal may comprise a single signal or may comprise multiple signals (e.g., one signal for each wavelength of light). An illustrative light drive signal is shown in FIG. 2A.

Figure 2A:
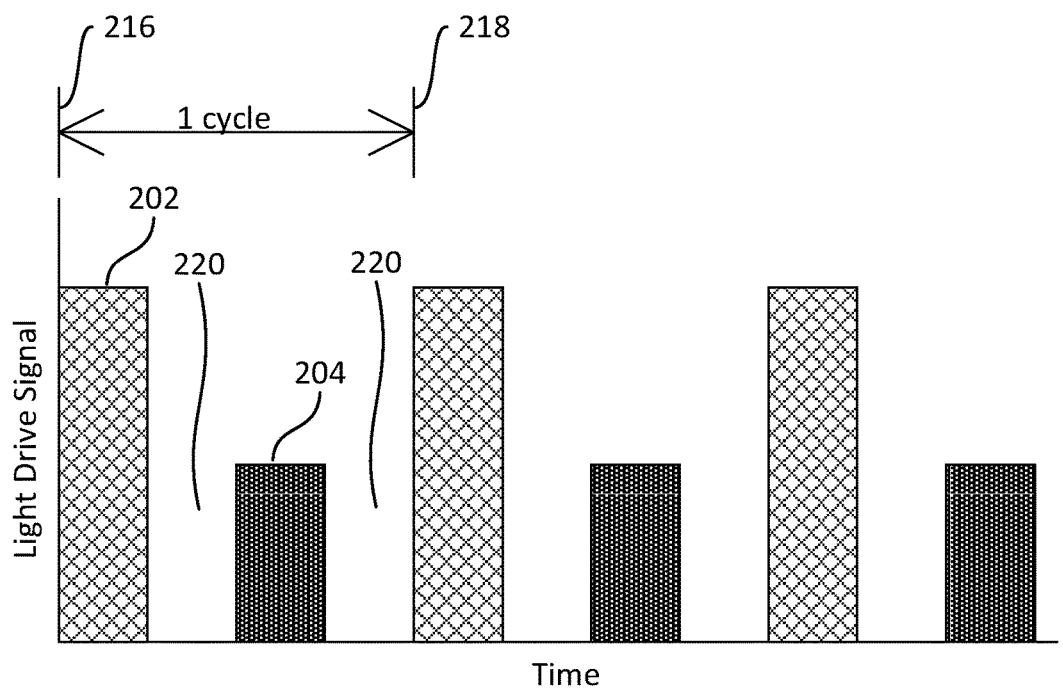
FIG. 2A shows an illustrative plot of a light drive signal in accordance with some embodiments of the present disclosure.

FIG. 2A shows an illustrative plot of a light drive signal including red light drive pulse 202 and IR light drive pulse 204 in accordance with some embodiments of the present disclosure. Light drive pulses 202 and 204 are illustrated as square waves. These pulses may include shaped waveforms rather than a square wave. Light drive pulses 202 and 204 may be generated, for example, by light drive circuit 120 under the control of control circuit 110. As used herein, drive pulses may refer to the high and low states of a shaped pulse, switching power or other components on and off, high and low output states, high and low values within a continuous modulation, other suitable relatively distinct states, or any combination thereof. The light drive signal may be provided to light source 130 to drive red and IR light emitters within light source 130. Light drive pulses 202 and 204 may have similar or different amplitudes. The amplitudes can be individually controlled by light drive circuit 120.

When the red and IR light sources are driven in this manner they emit pulses of light at their respective wavelengths into the tissue of a subject in order to generate sensor signals that include physiological information that physiological monitoring system 100 may process to calculate physiological parameters. It will be understood that the light drive amplitudes of FIG. 2A are merely exemplary and that any suitable amplitudes or combination of amplitudes may be used, and may be based on the light sources, the subject tissue, the determined physiological parameter, modulation techniques, power sources, any other suitable criteria, or any combination thereof.

The light drive signal of FIG. 2A may also include "off" periods 220 between the red and IR light drive pulses. "Off" periods 220 are periods during which no drive current may be applied to light source 130. "Off" periods 220 may be provided, for example, to prevent overlap of the emitted light, since light source 130 may require time to turn completely on and completely off. "Off" periods may also be referred to as dark periods, in that the emitters are dark or returning to dark during that period. The period from time 216 to time 218 may be referred to as a drive cycle. After time 218, the drive cycle may be repeated (e.g., as long as a light drive signal is provided to light source 130). It will be understood that the starting point of the drive cycle is merely illustrative and that the drive cycle can start at any location within FIG. 2A. It will be understood that the particular square pulses illustrated in FIG. 2A are merely exemplary and that any suitable light drive scheme is possible. For example, light drive schemes may include shaped pulses, sinusoidal modulations, time division multiplexing other than as shown, frequency division multiplexing, phase division multiplexing, any other suitable light drive scheme, or any combination thereof.

Referring back to FIG. 1, front end processing circuit 150 may receive a detection signal from detector 140 and provide one or more processed signals to back end processing circuit 170. The term "detection signal," as used herein, may refer to any of the signals generated within front end processing circuit 150 as it processes the output signal of detector 140. Front end processing circuit 150 may perform various analog and digital processing of the detector signal. One suitable detector signal that may be received by front end processing circuit 150 is shown in FIG. 2B.

Figure 2B:
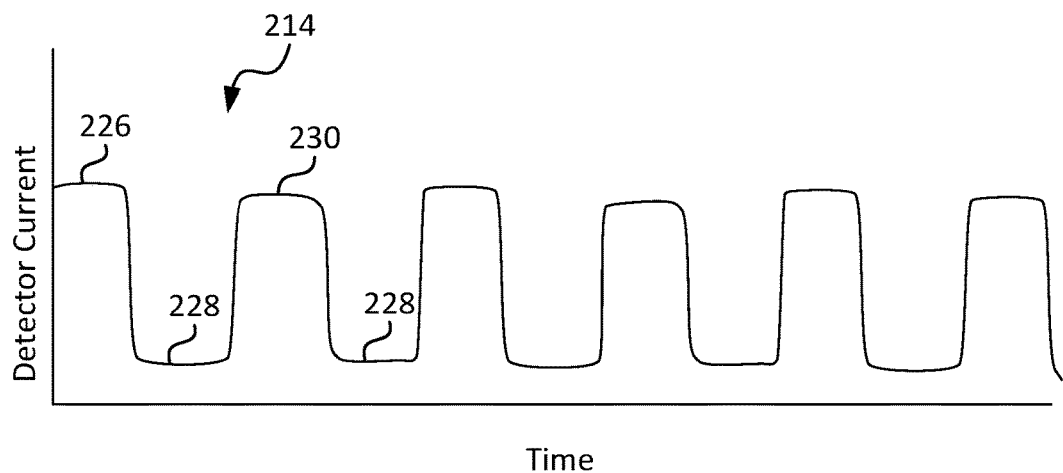
FIG. 2B shows an illustrative plot of a detector signal that may be generated by a sensor in accordance with some embodiments of the present disclosure.

FIG. 2B shows an illustrative plot of detector current waveform 214 that may be generated by a sensor in accordance with some embodiments of the present disclosure. The peaks of detector current waveform 214 may represent current signals provided by a detector, such as detector 140 of FIG. 1, when light is being emitted from a light source. The amplitude of detector current waveform 214 may be proportional to the light incident upon the detector. The peaks of detector current waveform 214 may be synchronous with drive pulses driving one or more emitters of a light source, such as light source 130 of FIG. 1. For example, detector current peak 226 may be generated in response to a light source being driven by red light drive pulse 202 of FIG. 2A, and peak 230 may be generated in response to a light source being driven by IR light drive pulse 204. Valleys 228 of detector current waveform 214 may be synchronous with periods of time during which no light is being emitted by the light source, or the light source is returning to dark, such as "off" periods 220. While no light is being emitted by a light source during the valleys, detector current waveform 214 may not fall all of the way to zero.

It will be understood that detector current waveform 214 as depicted may be an at least partially idealized representation of a detector signal, assuming near perfect light signal generation, transmission, and detection. It will be understood that an actual detector current will include amplitude fluctuations, frequency deviations, droop, overshoot, undershoot, rise time deviations, fall time deviations, other deviations from the ideal, or any combination thereof.

Referring back to FIG. 1, front end processing circuit 150, which may receive a one or more detection signals, such as detector current waveform 214, may include analog conditioning 152, analog-to-digital converter (ADC) 154, demultiplexer 156, digital conditioning 158, decimator/interpolator 160, and ambient subtractor 162.

Analog conditioning 152 may perform any suitable analog conditioning of the detector signal. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. In some embodiments, one or more gain settings may be used in analog conditioning 152 to adjust the amplification of the detector signal.

The conditioned analog signal may be processed by analog-to-digital converter 154, which may convert the conditioned analog signal into a digital signal. Analog-to-digital converter 154 may operate under the control of control circuit 110. Analog-to-digital converter 154 may use timing control signals from control circuit 110 to determine when to sample the analog signal. Analog-to-digital converter 154 may be any suitable type of analog-to-digital converter of sufficient resolution to enable a physiological monitor to accurately determine physiological parameters.

Demultiplexer 156 may operate on the analog or digital form of the detector signal to separate out different components of the signal. For example, detector current waveform 214 of FIG. 2B includes a red component corresponding to peak 226, an IR component corresponding to peak 230, and at least one ambient component corresponding to valleys 228. Demultiplexer 156 may operate on detector current waveform 214 of FIG. 2B to generate a red signal, an IR signal, a first ambient signal (e.g., corresponding to the ambient component corresponding to valley 228 that occurs immediately after the peak 226), and a second ambient signal (e.g., corresponding to the ambient component corresponding to valley 228 that occurs immediately after peak 230). Demultiplexer 156 may operate under the control of control circuit 110. For example, demultiplexer 156 may use timing control signals from control circuit 110 to identify and separate out the different components of the detector signal.

Digital conditioning 158 may perform any suitable digital conditioning of the detector signal. Digital conditioning 158 may include any type of digital filtering of the signal (e.g., low pass, high pass, band pass, notch, or any other suitable filtering), amplifying, performing an operation on the signal, performing any other suitable digital conditioning, or any combination thereof.

Decimator/interpolator 160 may decrease the number of samples in the digital detector signal. For example, decimator/interpolator 160 may decrease the number of samples by removing samples from the detector signal or replacing samples with a smaller number of samples. The decimation or interpolation operation may include or be followed by filtering to smooth the output signal.

Ambient subtractor 162 may operate on the digital signal. In some embodiments, ambient subtractor 162 may remove dark or ambient contributions to the received signal or signals.

The front end processing circuit 150 may be configured to take advantage of the full dynamic range of analog-to-digital converter 154. This may be achieved by applying one or more gains to the detection signal, by analog conditioning 152 to map the expected range of the signal to the full or close to full output range of analog-to-digital converter 154.

The components of front end processing circuit 150 are merely illustrative and any suitable components and combinations of components may be used to perform the front end processing operations.

Back end processing circuit 170 may include processor 172 and memory 174. Processor 172 may be adapted to execute software, which may include an operating system and one or more applications, as part of performing the functions described herein. Processor 172 may receive and further process sensor signals received from front end processing circuit 150. For example, processor 172 may determine one or more physiological parameters based on the received physiological signals. Processor 172 may include an assembly of analog or digital electronic components. Processor 172 may calculate physiological information. For example, processor 172 may compute one or more of fluid responsiveness, a blood oxygen saturation (e.g., arterial, venous, regional, or a combination thereof), pulse rate, respiration rate, respiration effort, blood pressure, hemoglobin concentration (e.g., oxygenated, deoxygenated, and/or total), any other suitable physiological parameters, or any combination thereof. Processor 172 may perform any suitable signal processing of a signal, such as any suitable scaling, band-pass filtering, adaptive filtering, closed-loop filtering, any other suitable filtering, and/or any combination thereof. Processor 172 may also receive input signals from additional sources not shown. For example, processor 172 may receive an input signal containing information about treatments provided to the subject from user interface 180. Additional input signals may be used by processor 172 in any of the calculations or operations it performs in accordance with back end processing circuit 170 or monitor 104.

Memory 174 may include any suitable non-transitory computer-readable media capable of storing information that can be interpreted by processor 172. In some embodiments, memory 174 may store calculated values, such as fluid responsiveness values, pulse rate, blood pressure, blood oxygen saturation, fiducial point locations or characteristics, initialization parameters, cardiac output, adaptive filter parameters, recommended amount of fluid to be administered, update characteristics, filter weights, any other calculated values, or any combination thereof, in a memory device for later retrieval. In some embodiments, memory 174 may store information regarding fluid responsiveness thresholds, blood oxygen saturation thresholds, regions of the subject being analyzed, amounts of fluid administered, and any combination thereof in a memory device for later retrieval. This information may be data or may take the form of computer-executable instructions, such as software applications, that cause a processor to perform certain functions and/or computer-implemented methods. Computer storage media may include volatile and non-volatile, removable and non-removable media implemented in any method or technology for storage of information such as computer-readable instructions, data structures, program modules, or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

Back end processing circuit 170 may be communicatively coupled with user interface 180 and communication interface 190.

User interface 180 may include user input 182, display 184, and speaker 186. User interface 180 may include, for example, any suitable device such as one or more medical devices (e.g., a medical monitor that displays various physiological parameters, a medical alarm, or any other suitable medical device that either displays physiological parameters or uses the output of back end processing 170 as an input), one or more display devices (e.g., monitor, personal digital assistant (PDA), mobile phone, tablet computer, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

User input 182 may include any type of user input device such as a keyboard, a mouse, a touch screen, buttons, switches, a microphone, a joy stick, a touch pad, or any other suitable input device. The inputs received by user input 182 can include information about the subject, such as age, weight, height, diagnosis, medications, treatments including fluid administered thereto, and so forth.

In an embodiment, the subject may be a medical patient and display 184 may exhibit a list of values which may generally apply to the patient, such as, for example, age ranges or medication families, which the user may select using user input 182. Additionally, display 184 may display, for example, an estimate of a subject's fluid responsiveness information, blood oxygen saturation, pulse rate information, respiration rate and/or effort information, blood pressure information, hemoglobin concentration information, cardiac output, any other parameters, and any combination thereof. Display 184 may also display an indication of treatment to be given to the subject, including, for example, an indication of whether or not to administer fluid, how much fluid to administer, an indication of the effectiveness of the treatment, any other information regarding fluid administration, and any combination thereof. Display 184 may include any type of display such as a cathode ray tube display, a flat panel display such as a liquid crystal display or plasma display, or any other suitable display device. Speaker 186 within user interface 180 may provide an audible sound that may be used in various embodiments, such as for example, sounding an audible alarm in the event that a patient's physiological parameters are not within a predefined normal range, or sounding an alarm in the event that the patient's fluid administration should be started or stopped.

Communication interface 190 may enable monitor 104 to exchange information with external devices. Communication interface 190 may include any suitable hardware or hardware and software, which may allow monitor 104 to communicate with electronic circuitry, a device, a network, a server or other workstations, a display, or any combination thereof. In some embodiments, communications interface 190 is coupled to a sensor input port or a digital communications port of an external device. Communication interface 190 may include one or more receivers, transmitters, transceivers, antennas, plug-in connectors, ports, communications buses, communications protocols, device identification protocols, any other suitable hardware and software, or any combination thereof. Communication interface 190 may be configured to allow wired communication, wireless communication, or both. In some embodiments, communications interface 190 may enable monitor 104 to exchange information with external devices such as a regional oximeter, a pulse oximeter, any other suitable external devices, and any combination thereof. For example, communications interface 190 may receive oxygen saturation and/or fluid responsiveness information from any of the foregoing external devices, any other suitable devices, or any suitable combination thereof. In some embodiments, communications interface 190 may enable monitor 104 to control external devices configured to automatically administer fluid to a subject. For example, communications interface 190 may receive a signal indicative of fluid administration to be provided to the subject from processing equipment and may send this signal to a fluid administration mechanism to carry out the fluid administration. In some embodiments, communications interface 190 may enable monitor 104 to exchange information with a multi-parameter monitor or a calibration device. The calibration device may be powered by monitor 104, a battery, or by a conventional power source such as a wall outlet. In some embodiments, the calibration device is completely integrated within monitor 104. In some embodiments, the calibration device may include a manual input device used by a user to manually input reference signal measurements obtained from some other source (e.g., an external invasive or non-invasive physiological measurement system).

It will be understood that the components of physiological monitoring system 100 that are shown and described as separate components are shown and described as such for illustrative purposes only. In some embodiments the functionality of some of the components may be combined in a single component. For example, the functionality of front end processing circuit 150 and back end processing circuit 170 may be combined in a single processor system. Additionally, in some embodiments the functionality of some of the components of monitor 104 shown and described herein may be divided over multiple components. For example, some or all of the functionality of control circuit 110 may be performed in front end processing circuit 150, in back end processing circuit 170, or both. In other embodiments, the functionality of one or more of the components may be performed in a different order or may not be required. In an embodiment, all of the components of physiological monitoring system 100 can be realized in processor circuitry. In some embodiments, any of the components of FIG. 1 may be referred to collectively as processing equipment. It will understood that, as used herein, the term "circuit" refers to structure such as, for example, an electronic circuit, a portion of an electronic circuit, or a combination of electronic circuits.

As described above, respiratory variation in the arterial blood pressure waveform is known to be a good predictor of a subject's fluid responsiveness. In particular, the PPV of a subject is known to be a good predictor of fluid responsiveness, but, as described above, requires invasive procedures to determine. Accordingly, determining respiratory variation in a PPG signal from a pulse oximeter may provide a non-invasive alternative to determining the PPV of a subject. Determination of fluid responsiveness in accordance with the present disclosure will be discussed with reference to FIG. 3 below. Although a PPG signal from a pulse oximeter is used to illustrate embodiments of the present disclosure, it will be understood that the techniques described herein are not limited to PPG signals and pulse oximeters and may be applied to any suitable physiological signals and monitoring devices.

Figure 3:
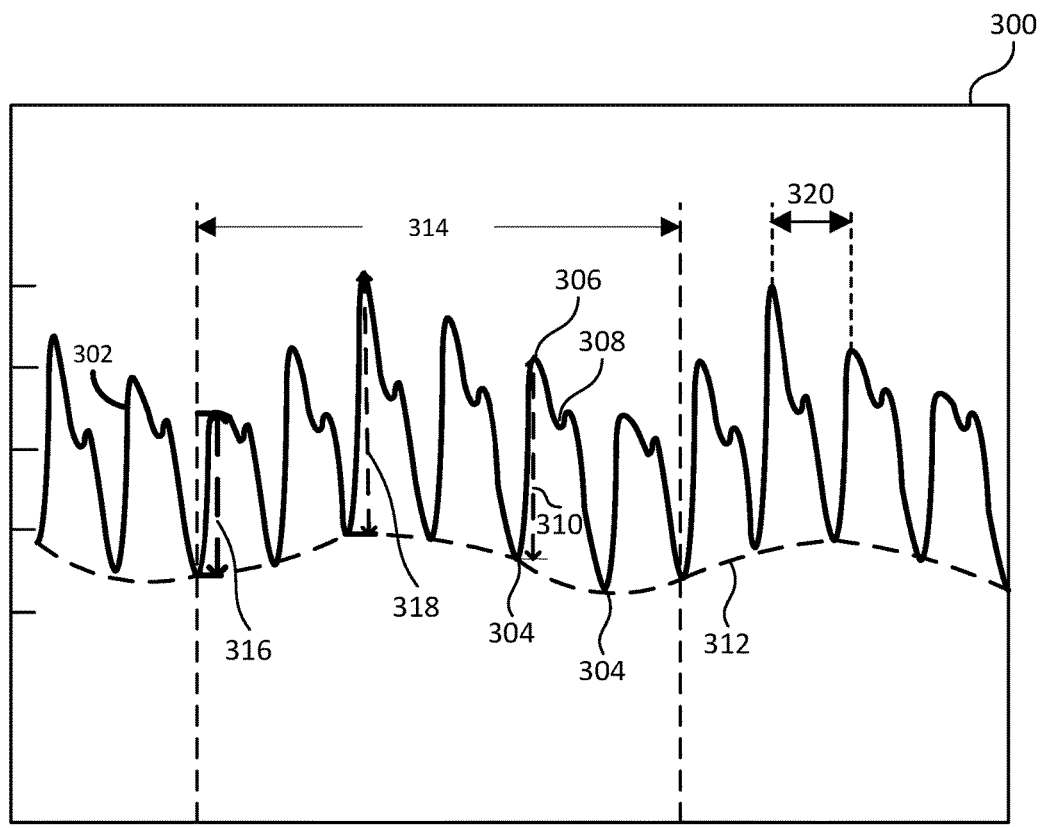
FIG. 3 shows an illustrative plot of a PPG waveform reflecting respiratory modulations in accordance with some embodiments of the present disclosure.

FIG. 3 shows an illustrative plot 300 of PPG waveform 302 reflecting respiratory modulations in accordance with some embodiments of the present disclosure. PPG waveform 302 may be generated, for example, by system 100 of FIG. 1. As illustrated, PPG waveform 302 represents the absorption of light by a subject's tissue over time. PPG waveform 302 includes pulses where the absorption of light increases due to the increased volume of blood in the arterial blood vessel due to cardiac pulses. In some embodiments, pulses may be identified between adjacent valleys 304 and as illustrated may include a peak 306 and a dicrotic notch 308. The pulses include an upstroke between the first valley and the main peak. For example, an upstroke is depicted in FIG. 3 between the first valley 304 and peak 306. The amplitude of this upstroke is depicted as amplitude 310 measured from the first valley 304 to peak 306. Other amplitude values may be derived from the PPG waveform, such as a downstroke amplitude, average amplitude, or area under the pulse. In some embodiments, the amplitude of a pulse may be determined by subtracting a minimum value of PPG waveform 302 from a maximum value of PPG waveform 302 within a segment of PPG waveform 302 that generally corresponds to the period of a pulse. PPG waveform 302 also includes a varying baseline 312. PPG waveform 302 modulates above baseline 312 due to the pulses.

For most subjects, the PPG signal is affected by the subject's respiration, i.e. inhaling and exhaling, resulting in certain respiration modulations in the PPG waveform. FIG. 3 illustrates respiration modulations in PPG waveform 302 as a result of the subject's inhaling and exhaling. One type of respiratory modulation is the modulation of baseline 312 of PPG waveform 302. The effect of the subject's breathing in and out causes the baseline of the waveform 302 to move up and down, cyclically, with the subject's respiration. The baseline may be tracked by following any fiducial of PPG waveform 302, such as the peaks 306, valleys 304, dicrotic notches 308, median value, or any other fiducials. A second type of respiration-induced modulation of PPG waveform 302 is the modulation of pulse amplitudes. As the patient breathes in and out, the amplitude of the pulses decrease and increase, with larger amplitudes tending to coincide with the top of the baseline shift, and smaller amplitudes tending to coincide with the bottom of the baseline shift (though the larger and smaller amplitudes do not necessarily fall at the top and bottom of the baseline shift). A third respiratory type of modulation is the modulation of period 320 between pulses (also referred to as frequency modulation). Each of these modulations may be referred to as a respiratory component of PPG waveform 302, or a respiratory-induced modulation of PPG waveform 302. It should be noted that a particular individual may exhibit only the baseline modulation, or only the amplitude modulation, or only the frequency modulation, or any combination thereof. As referred to herein, a respiratory component of the PPG waveform 302 includes any one of these respiratory-induced modulations of PPG waveform 302, a measure of these modulations, or a combination of them.

The respiratory modulations of PPG waveform 302 can be affected by a subject's fluid status. For example, a hypovolemic subject may exhibit relatively larger respiratory variations of PPG waveform 302. When a subject loses fluid, the subject may have decreased cardiac output or stroke volume, which tends to increase the respiratory variations present in the subject's PPG waveform. Specifically, the baseline modulation, amplitude modulation, and frequency modulation may become more pronounced. Thus, larger respiratory modulations may indicate that the subject will respond favorably to fluid loading, whereas smaller respiratory modulations may indicate that a patient may not respond favorably to fluid loading. The respiratory modulations of PPG waveform 302 may be identified and used to determine a subject's fluid responsiveness.

In some embodiments, a physiological monitor receives a PPG signal and determines a parameter indicative of fluid responsiveness based on the PPG signal. In some embodiments, the parameter indicative of fluid responsiveness is a measure of a subject's likely response to fluid therapy. In some embodiments, the parameter indicative of fluid responsiveness is a metric that reflects a degree of respiratory variation of the PPG signal. One example of a parameter indicative of fluid responsiveness is a measure of the amplitude modulations of the PPG signal, such as Delta POP (DPOP or ΔPOP). Another example of a parameter indicative of fluid responsiveness is a measure of the baseline modulation of the PPG signal. In some embodiments, other suitable metrics or combinations of metrics may be used to assess the respiratory modulation of the PPG signal. For example, a parameter indicative of fluid responsiveness may be based on the amplitudes or areas of acceptable pulses within a particular time frame or window. For example, as illustrated in FIG. 3, minimum amplitude 316 of the pulses within respiratory period 314 may be subtracted from maximum amplitude 318 within respiratory period 314 and then divided by an average or mean value of minimum amplitude 316 and maximum amplitude 318. In some embodiments, a parameter indicative of fluid responsiveness may be derived from the period or frequency of pulses within a time frame or window. For example, a modulation or variation in the period or frequency among two or more cardiac pulses may be used to derive a parameter indicative of fluid responsiveness. In general, the parameter indicative of fluid responsiveness may be based on one or more respiratory variations exhibited by the PPG waveform 302. Further, a parameter indicative of fluid responsiveness may be determined through the use of wavelet transforms, such as described in United States Patent Application Publication No. 2010/0324827, entitled "Fluid Responsiveness Measure," which is hereby incorporated by reference in its entirety.

In some embodiments, DPOP is used as the parameter indicative of fluid responsiveness. In some embodiments, the DPOP metric can be calculated from PPG waveform 302 for a particular time window as follows:

$$DPOP=(AMP_{max}-AMP_{min})/AMP_{ave}, \quad (1)$$

where $AMP_{max}$ represents the maximum amplitude (such as maximum amplitude 318 in FIG. 3) during a time window (such as respiratory period 314 in FIG. 3), $AMP_{min}$ represents the minimum amplitude (such as minimum amplitude 316 in FIG. 3) during the time window, and $AMP_{ave}$ is the average of the two, as follows:

$$AMP_{ave}=(AMP_{max}+AMP_{min})/2 \quad (2)$$

In some embodiments, $AMP_{max}$ and $AMP_{min}$ may be measured at other locations of the PPG, such as within or along a pulse. DPOP is a measure of the respiratory variation in the AC portion of the PPG signal. DPOP is a unit-less value, and in some embodiments can be expressed as a percentage. In some embodiments, a scaling factor may be applied to DPOP so that DPOP more closely corresponds to PPV. For example, the scaling factor can be applied to the terms in the numerator or denominator of equation 1, or to the computed DPOP value. In some embodiments, respiratory period 314 is one respiratory cycle (inhalation and exhalation). In some embodiments, respiratory period 314 is a fixed duration of time that approximates one respiratory cycle, such as 5 seconds, 10 seconds, or any other suitable duration. In some embodiments, respiratory period 314 may be adjusted dynamically based on the subject's calculated or measured respiration rate, so that the period is approximately the same as one respiratory cycle period. In some embodiments, a signal turning point detector may be used to identify the maximum and minimum points in the PPG signal, in order to calculate the upstroke amplitudes. In some embodiments, $AMP_{ave}$ may be a filtered version of the PPG, such as a low-pass version of the PPG signal.

Figure 4:
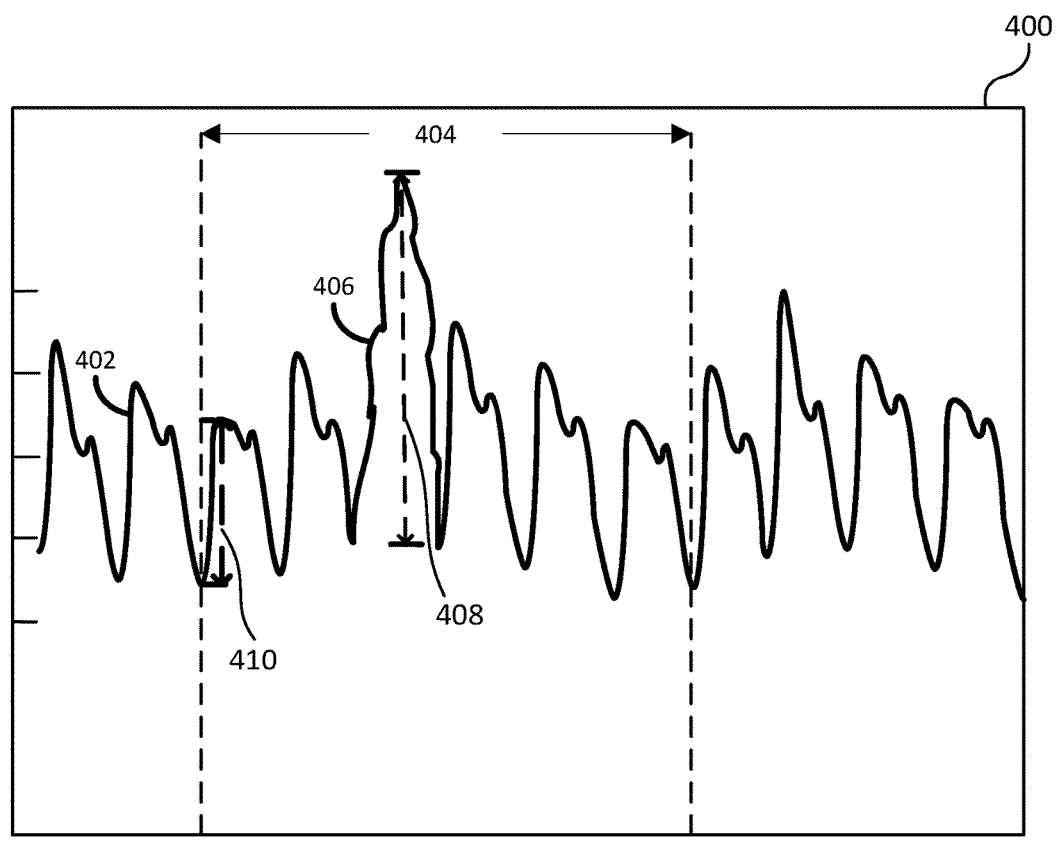
FIG. 4 shows an illustrative plot of a PPG waveform exhibiting a period of noise in accordance with some embodiments of the present disclosure.

As described above, PPG signals used to calculate DPOP may be susceptible to noise. FIG. 4 shows an illustrative plot 400 of a PPG waveform 402 exhibiting a period of noise in accordance with some embodiments of the present disclosure. As can be seen in plot 400, PPG waveform 402 is similar to PPG waveform 302 of FIG. 3, except that the waveform exhibits noise in the vicinity of pulse 406. As a result, amplitude 408 associated with pulse 406 is erroneously large. If DPOP is calculated from PPG waveform 402 over respiratory period 404 using Eqs. 1-2, the maximum computed amplitude (i.e., $AMP_{max}$) value used for that period would be the erroneous large amplitude 408 and the minimum computed amplitude (i.e. $AMP_{min}$) value used for that period would be amplitude 410. It will be understood that due to the use of the erroneously large amplitude 408 as the $AMP_{max}$ value, the DPOP value calculated from respiratory period 404 would be erroneously large relative to DPOP calculated from previous respiratory periods. It will be understood that in some instances an erroneous amplitude calculated due to noise may be the minimum computed amplitude over a respiratory period or an amplitude between the maximum computed amplitude and the minimum amplitude. However, due to the generally large-scale effect of such noise on signals such as PPG signals, it is much more likely that an erroneous amplitude computed due to noise will be the maximum computed amplitude over a respiratory period. Moreover, the erroneous amplitude is likely to be of a value significantly larger than the true (i.e. values not substantially affected by noise) maximum computed amplitudes in its vicinity, and thus have a significant effect on the computed DPOP value.

In some embodiments, it is desirable to determine the parameter indicative of fluid responsiveness by averaging the parameter as calculated in accordance with any of the embodiments described above over a second time window. For example, if DPOP is used as the parameter indicative of fluid responsiveness, and is calculated over a fixed duration of 10 seconds, it may be desirable to average the plurality of DPOP calculations performed over a fixed window of 120 seconds, effectively taking the average of 12 DPOP calculations to yield a parameter indicative of the subject's fluid responsiveness. While averaging the parameter in this manner—giving a fixed equal weight to a certain number of previous instantaneous DPOP calculations—may mitigate the effect of erroneous amplitudes computed due to noise, it may still cause erroneous DPOP values to be reported.

Figure 5:
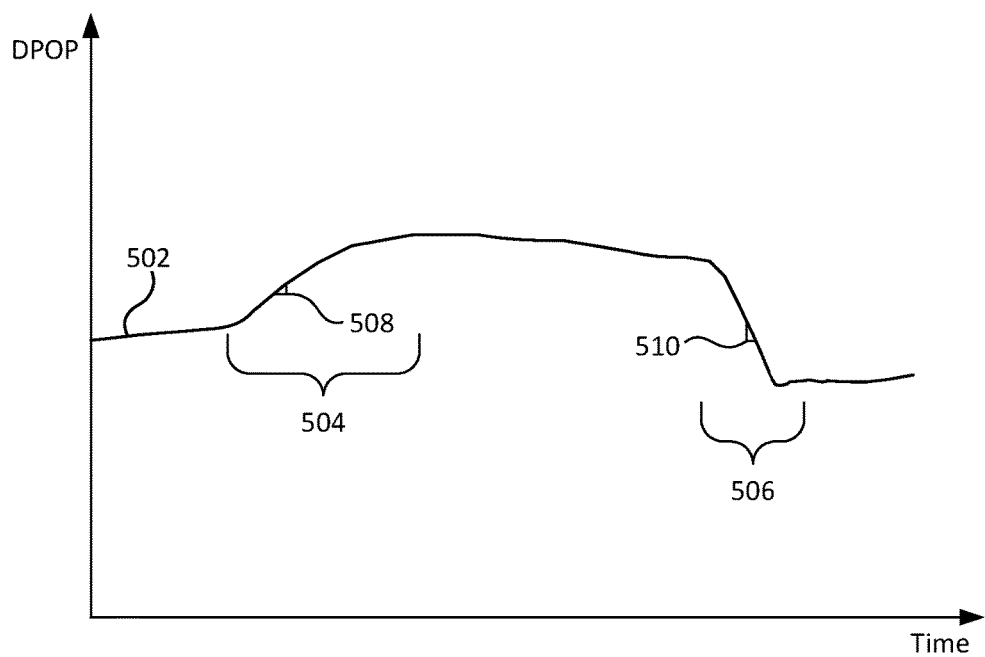
FIG. 5 shows an illustrative plot of a fluid responsiveness parameter over time in accordance with some embodiments of the present disclosure.

Accordingly, in some embodiments, in order to mitigate the effect of erroneously large instantaneous DPOP values used to determine the DPOP value used for diagnosis, DPOP is determined with a response time that is based on whether DPOP is increasing or decreasing. In some embodiments, an update characteristic may be selected based on whether the instantaneous DPOP values are increasing or decreasing, and the DPOP value used for diagnosis may be determined based on the update characteristic and one or more previous DPOP values. In some embodiments, the update characteristic may be an amount of change to be added to a previously reported DPOP value, where the amount of change may be greater when the instantaneous DPOP values are decreasing or stable than when the instantaneous DPOP values are increasing. For example, the rate of change of the DPOP value used for diagnosis may be differentiated and the allowable rate of change of the DPOP value used for diagnosis may be controlled based on the polarity of the rate of change. For example, the allowable rate of change of the DPOP value used for diagnosis may be set higher when DPOP is reducing in value, but lower when DPOP is increasing in value. FIG. 5 shows an illustrative plot 500 of a DPOP value 502 used for diagnosis over time in accordance with some embodiments of the present disclosure. It can be seen in FIG. 5 that during time period 504, where the DPOP value used for diagnosis 502 is increasing, the rate of change has been limited to the maximum slope 508, and during time period 506, where the DPOP value used for diagnosis 502 is decreasing, the rate of change has been limited to the minimum slope 510. It can also be seen in FIG. 5 that the absolute value of minimum slope 510 is higher than maximum slope 508 in order to mitigate the effect of erroneously large instantaneous DPOP values resulting from noise-induced erroneously large maximum computed amplitudes.

In accordance with embodiments of the present disclosure, the reported DPOP value used for diagnosis may be a function of the history of instantaneously calculated DPOP values. For example, instantaneous values of DPOP may be calculated according to Eqs. 1-2, and the reported DPOP value used for diagnosis may be a function of the historical calculated instantaneous values. In some embodiments, the reported DPOP value may be a low pass filtered version of instantaneous DPOP values of the form:

$$DPOP(t)_{reported} = w \cdot DPOP_{inst} + (1-w) \cdot DPOP(t-1)_{reported} \quad (3)$$

where $DPOP(t)_{reported}$ is the current reported DPOP value, $DPOP(t-1)_{reported}$ is the most recent previously reported DPOP value, $DPOP_{inst}$ is the instantaneously calculated DPOP value, and w is a weight given to $DPOP_{inst}$. In some embodiments, $DPOP_{inst}$ may be an average of any suitable number of instantaneously calculated DPOP values. For example, as described above, $DPOP_{inst}$ may be an average of 12 calculations of DPOP, each calculation calculated over a fixed duration of 10 seconds.

It will be understood that, in accordance with embodiments of the present disclosure, the weight w may be used to govern the rate at which the reported DPOP value may change based on whether DPOP is increasing or decreasing. In some embodiments, w may be limited based on the polarity of the difference $DPOP_{inst}$ and $DPOP(t-1)_{reported}$. For example, one constant value may be selected for w if $DPOP_{inst}$ is greater than $DPOP(t-1)_{reported}$, and a different, higher constant value may be selected for w, if $DPOP_{inst}$ is less than $DPOP(t-1)_{reported}$. In some embodiments, w may be a dynamic function of $DPOP_{inst}$ and $DPOP(t-1)_{reported}$ to produce an adaptive rate of change of $DPOP_{reported}$. For example, rather than selecting a value for w from a set of constants, w may be defined in terms of $DPOP_{inst}$ and $DPOP(t-1)_{reported}$. In one instance, w may be defined by a function that decreases as the value of $DPOP_{inst} - DPOP(t-1)_{reported}$ increases. In other words, the larger a particular $DPOP_{inst}$ is when compared to $DPOP(t-1)_{reported}$, the less weight is given to that particular $DPOP_{inst}$, since it is more likely to be due to erroneous amplitudes caused by noise. Accordingly, w can vary depending on whether $DPOP_{inst}$ is greater or less than $DPOP(t-1)_{reported}$ and depending on the amount of difference between $DPOP_{inst}$ and $DPOP(t-1)_{reported}$. In this way, the updated reported value of DPOP may not be overly affected by instantaneous values of DPOP that are susceptible to be affected by noise, particularly when the instantaneous value is substantially higher than the last reported value. It will be understood that varying w in this way also avoids placing a strict limit on the rate of change of the reported value of DPOP, thus allowing for the possibility of DPOP changes due to actual variability of a subject's fluid responsiveness.

In some embodiments, the effects of noise in $DPOP_{inst}$ may be minimized by quantizing the change in the reported DPOP value. For example, $DPOP_{reported}$ may be represented by the following expression in terms of the previous reported DPOP and a quantized change α:

$$DPOP(t)_{reported} = \alpha + DPOP(t-1)_{reported} \quad (4)$$

It will be understood that α may be defined in a number of ways in accordance with embodiments of the present disclosure. In some embodiments, α may be dependent upon a comparison between $DPOP(t-1)_{reported}$ and $DPOP_{inst}$. For example, α may be a set of constants defined as follows:

$$\alpha = 0 \text{ for } DPOP_{inst} = DPOP(t-1)_{reported} \quad (5)$$

$$\alpha = y \text{ for } DPOP_{inst} < DPOP(t-1)_{reported} \quad (6)$$

$$\alpha = x \text{ for } DPOP_{inst} > DPOP(t-1)_{reported}, \quad (7)$$

where x and y are constants. Thus, the amount that the reported DPOP value can change from one calculation to the next is selected from a set of constants, where the constants are selected based on a comparison between $DPOP_{inst}$ and $DPOP(t-1)_{reported}$. Accordingly, in some embodiments, regardless of the amount of difference between $DPOP_{inst}$ and $DPOP(t-1)_{reported}$, the reported DPOP value will only change a certain fixed amount upwards or downwards or not change at all. It will be understood that x and y may be determined such that the reported DPOP value may change by a larger amount when $DPOP_{inst}$ is less than $DPOP(t-1)_{reported}$, than when $DPOP_{inst}$ is greater than $DPOP(t-1)_{reported}$. For example, y may be a negative value and x may be a positive constant value, and the magnitude of y may be larger than x. In this way, the reported DPOP value may limit the effect of erroneously increased instantaneous DPOP values likely due to noise while maintaining an appropriate effect of relatively large decreases in instantaneous DPOP values that are less likely due to noise.

In some embodiments, α may be a set of functions dependent upon the difference between $DPOP(t-1)_{reported}$ and $DPOP_{inst}$. For example, α may be defined as follows:

$$\alpha = ((DPOP_{inst} - DPOP(t-1)_{reported}) - threshold) \cdot z + threshold \quad (8)$$

for $DPOP_{inst} - DPOP(t-1)_{reported} > threshold$, and $$\alpha = (DPOP_{inst} - DPOP(t-1)_{reported}) \quad (9)$$

for $DPOP_{inst} - DPOP(t-1)_{reported} \leq threshold$,
where the threshold is a value determined likely to be due to noise and z is a constant between 0 and 1. Thus, the amount that the reported DPOP value will change from one calculation to the next is selected from a set of functions, where the functions are selected based on a comparison between the evaluated expression $DPOP_{inst} - DPOP(t-1)_{reported}$ and a threshold. In some embodiments, the threshold may be an empirically determined value. For example, the threshold may be a value above which the difference between $DPOP_{inst}$ and $DPOP(t-1)_{reported}$ has been found to be more likely to be due to noise. Accordingly, when $DPOP_{inst}$ is not so much higher than $DPOP(t-1)_{reported}$ so as to be likely physiological (i.e., $DPOP_{inst}-DPOP(t-1)_{reported} \leq$ threshold), the change in the reported DPOP value may simply be selected as the difference between the previous reported DPOP value and the instantaneous DPOP value as described in Eq. 9. When $DPOP_{inst}$ is much higher than $DPOP(t-1)_{reported}$ so as to be likely due to noise (i.e., $DPOP_{inst}-DPOP(t-1)_{reported}>$threshold), the change in the reported DPOP value may be modified or reduced. For example, as shown in Eq. 8, the amount that the reported DPOP value may change above the threshold amount may be reduced by multiplying it by the constant z which may be set to a value between 0 and 1. In other words, the reported DPOP value may only increase a small amount above the threshold. It will be understood that the use of a set of functions dependent upon the difference between $DPOP(t-1)_{reported}$ and $DPOP_{inst}$ to define the amount of change α, such as equations 8 and 9, allows the reported DPOP to change freely based on the amount of change between the instantaneous DPOP and the reported DPOP value except when it is likely that the change is due to noise, as opposed to setting a fixed amount of change that only considers what direction the change occurs in.

In some embodiments, the effects of noise in $DPOP_{inst}$ may be minimized by reducing the change in $DPOP_{reported}$ by a reduction factor. In some embodiments, $DPOP_{reported}$ may be represented by the following expression in terms of the previous reported value $DPOP(t-1)_{reported}$, $DPOP_{inst}$, and a reduction factor β as follows:

$$DPOP(t)_{reported} = \beta \cdot (DPOP_{inst} - DPOP(t-1)_{reported}) + DPOP(t-1)_{reported}. \quad (10)$$

In some embodiments, the reduction factor β may be defined based on the difference between $DPOP_{inst}$ and $DPOP(t-1)_{reported}$. For example, β may be defined as follows:

$$\beta = y \text{ for } DPOP_{inst} - DPOP(t-1)_{reported} > \text{threshold} \quad (11)$$

$$\beta = x \text{ for } DPOP_{inst} - DPOP(t-1)_{reported} \leq \text{threshold}, \quad (12)$$

where the threshold is a constant greater than 0 that indicates a large rise in $DPOP_{inst}$ and x and y are constants less than 1, with x greater than y. Thus, the amount that the reported DPOP value will change may be controlled by multiplying the difference between $DPOP_{inst}$ and $DPOP(t-1)_{reported}$ by a selected one of a set of constant reduction factors β, where the constant reduction factor is selected based on a comparison between the evaluated expression $DPOP_{inst}-DPOP(t-1)_{reported}$ and a threshold. In some embodiments, the threshold may be an empirically determined value. For example, the threshold may be a value above which the difference between $DPOP_{inst}$ and $DPOP(t-1)_{reported}$ has been found likely to be due to noise. Accordingly, when $DPOP_{inst}$ is not so much higher than $DPOP(t-1)_{reported}$ so as to be likely physiological (i.e., $DPOP_{inst}-DPOP(t-1)_{reported} \leq$threshold), the difference between $DPOP_{inst}$ and $DPOP(t-1)_{reported}$ may be reduced by multiplying the difference by the constant x which may be less than 1, and when $DPOP_{inst}$ is much higher than $DPOP(t-1)_{reported}$ so as to be likely due to noise (i.e., $DPOP_{inst}-DPOP(t-1)_{reported}>$threshold), the difference may be reduced even more by multiplying the difference by the constant y which is also less than 1 and smaller than x.

It will be understood that the embodiments described above may generate a reported DPOP value which both slowly reacts to noise and quickly responds back to true DPOP values after a noise event. In some embodiments, the rate of change of the reported DPOP value may be allowed to increase over time when it is more likely a real change in DPOP is occurring as opposed to an increase due to noise. In some embodiments, the amount of change of the reported DPOP value may be controlled using any of the techniques above or any combination thereof, but may be allowed to increase based on the confidence in the change in DPOP. For example, any suitable noise metric may be calculated to determine if there is noise in the PPG signal (such as a signal-to-noise metric), and if the metric indicates that the signal is relatively free from noise, any of the weights, the amounts of change, or the reduction factors described above with respect to Eqs. (3)-(12) may be modified to allow greater increases in the reported DPOP value. For instance, when the noise metric indicates the signal is not noisy, the instantaneous DPOP value may be given a greater weight, or the amount of change may be set to a higher constant or multiplied by a lower reduction factor. In some embodiments, the amount of change of the reported DPOP value may be controlled using any of the techniques above or any combination thereof, but may be allowed to increase as the time elapsed since the change increases. For example, if the instantaneous DPOP value remains stable at a higher value after a substantial increase for a certain period of time, the amount of change, or the reduction factors described above with respect to Eqs. (3)-(12) may be modified to allow greater increases in the reported DPOP value. Accordingly, it will be seen that in the above embodiments, a non-linear limit to the rate of change of the reported DPOP value may be set, since, in addition to controlling the amount of change in accordance with Eqs. (3)-(12) above, the amount of change may increase or decrease due to confidence, elapsed time since the change, or any other suitable factor.

Figure 6:
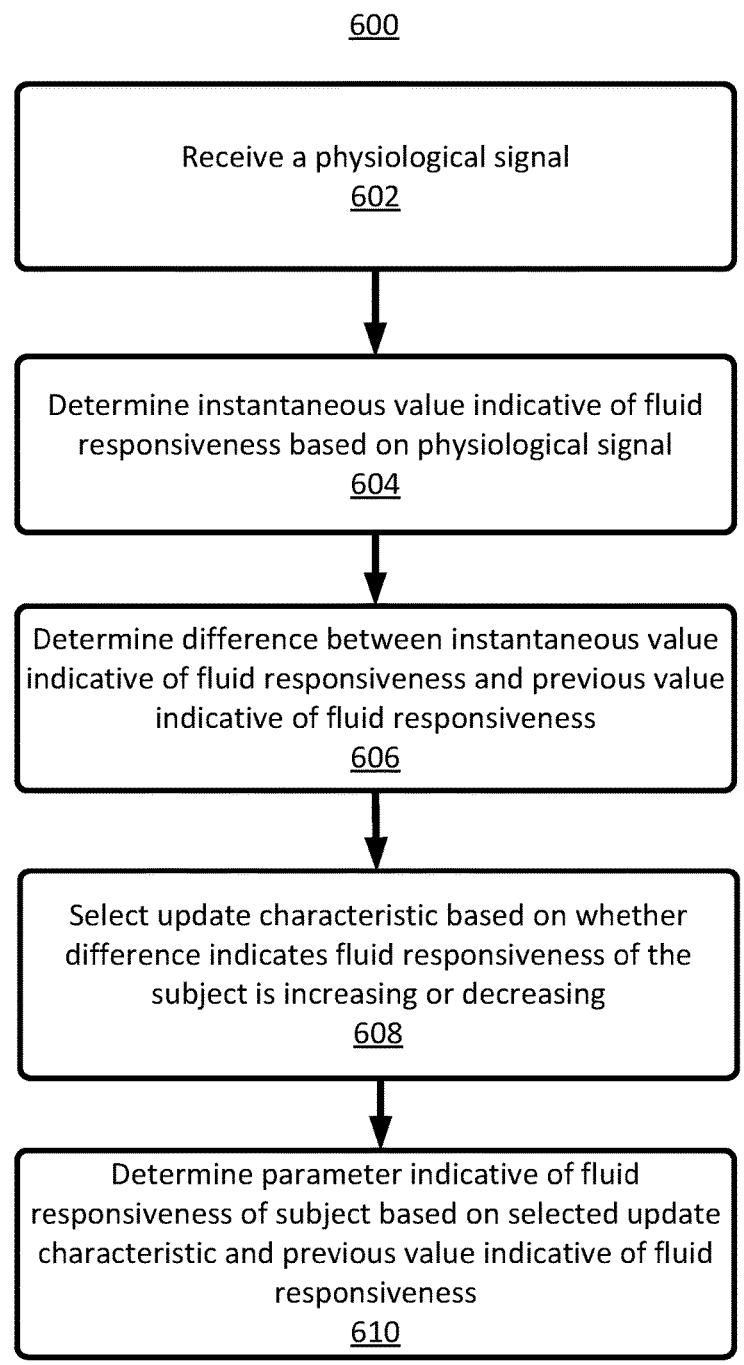
FIG. 6 shows an illustrative flow diagram for determining fluid responsiveness in accordance with some embodiments of the present disclosure.

FIG. 6 shows an illustrative flow diagram 600 for determining fluid responsiveness in accordance with some embodiments of the present disclosure. Although exemplary steps are described therein, it will be understood that one or more steps may be omitted and that any suitable additional steps may be added for determining fluid responsiveness. Although the steps described herein may be performed by any suitable device or system, in an exemplary embodiment, the steps may be performed by monitoring system 100 of FIG. 1, processing equipment thereof, any components and modules thereof, and any combination thereof.

Referring to FIG. 6, at step 602, the processing equipment may receive a physiological signal. The physiological signal may be indicative of light attenuated by a subject. For example, the physiological signal may include a PPG signal received from a pulse oximeter. In some embodiments the physiological signal may include a PPV signal or a physiological signal indicative of a subject's PPV. In some embodiments, the physiological signal may be received from one or more sensors of the physiological monitoring system, from external sensors, from other suitable sources internal or external of the physiological monitoring system, or from any suitable combination thereof. For example, processing equipment may receive a physiological signal from sensor 102 as described above with respect to FIG. 1.

At step 604, the processing equipment may determine an instantaneous value indicative of fluid responsiveness based on the physiological signal received in step 602. The processing equipment may determine the instantaneous value indicative of fluid responsiveness in accordance with any of the above-described methods. In some embodiments, processing equipment may determine the instantaneous value indicative of fluid responsiveness based on a PPG signal received from a pulse oximeter sensor. For example, processing equipment may determine the instantaneous value indicative of fluid responsiveness based on a PPG signal indicative of IR light absorbed by a subject, a PPG signal indicative of red wavelength light absorbed by a subject, or any other suitable PPG signal. In some embodiments, processing equipment may determine the instantaneous value indicative of fluid responsiveness based on respiratory variations identified in the physiological signal received in step 602. For example, processing equipment may determine the instantaneous value indicative of fluid responsiveness by determining a plurality of amplitudes in a physiological signal and by identifying maximum and minimum amplitudes during a time window indicative of a respiratory cycle and dividing a difference between the amplitudes by an average of the amplitudes. For example, the fluid responsiveness parameter may be determined based on equations (1)-(2) used to calculate DPOP as described above. In some embodiments, processing equipment may determine the instantaneous value indicative of fluid responsiveness by averaging a series of values determined based on equations (1)-(2). For example, processing equipment may determine the instantaneous value indicative of fluid responsiveness by taking the average of 12 DPOP calculations performed over a fixed window of 120 seconds.

At step 606, the processing equipment may determine a difference between the instantaneous value indicative of fluid responsiveness determined in step 604 and a previous value indicative of fluid responsiveness. In some embodiments, processing equipment may determine the difference by comparing the instantaneous value indicative of fluid responsiveness determined in step 604 to a previously calculated value indicative of fluid responsiveness. In some embodiments, the previously calculated value indicative of fluid responsiveness may be a previous instantaneous value indicative of fluid responsiveness. In some embodiments, the previously calculated value indicative of fluid responsiveness may be an average of one or more previous instantaneous values indicative of fluid responsiveness. In some embodiments, the previously calculated value indicative of fluid responsiveness may be a previously reported value. For example, the previously reported value may be the last value output on the display by the physiological monitor. In some embodiments, the difference may be an amount of difference. For example, processing equipment may determine an amount of difference by subtracting a previously calculated value indicative of fluid responsiveness from the instantaneous value indicative of fluid responsiveness determined at step 604. In some embodiments, processing equipment may compare the amount of difference to a threshold indicative of noise. For example, the processing equipment may subtract a previously calculated value indicative of fluid responsiveness from the instantaneous value indicative of fluid responsiveness and compare the difference to a threshold.

At step 608, the processing equipment may select an update characteristic based on whether the difference indicates that the fluid responsiveness of the subject is increasing or decreasing. In some embodiments, the update characteristic may be a weight corresponding to the instantaneous value indicative of fluid responsiveness. For example, the processing equipment may select one of a set of constant weights corresponding to the instantaneous value indicative of fluid responsiveness based on whether the difference determined at step 606 is positive or negative. As another example, the processing equipment may select a weight corresponding to the instantaneous value indicative of fluid responsiveness by evaluating a function based on the difference determined at step 606 between the instantaneous value indicative of fluid responsiveness and the previous value indicative of fluid responsiveness. In some embodiments, the update characteristic may be an amount of change to be added to a previously reported value indicative of fluid responsiveness. In some embodiments, the amount of change may be a constant amount of change selected by the processing equipment based on the comparison made at step 606 between the instantaneous value indicative of fluid responsiveness and the previous value indicative of fluid responsiveness. For example, the amount of change may be the quantized change $\alpha$ as defined above by Eqs. (5)-(7). In some embodiments, the amount of change may be an expression selected by the processing equipment based on the comparison between the difference made at step 606 of the instantaneous value indicative of fluid responsiveness and the previous value indicative of fluid responsiveness and a threshold. For example, the amount of change may be the quantized change $\alpha$ as defined above by Eqs. (8)-(9). In some embodiments, the update characteristic may be a reduction factor applied to an amount of change. In some embodiments, the reduction factor may be a constant selected by the processing equipment based on the comparison between the difference of the instantaneous value indicative of fluid responsiveness and the previous value indicative of fluid responsiveness determined at step 606 and a threshold. For example, the reduction factor may be the reduction factor $\beta$ as defined above by Eqs. (10)-(12). In some embodiments, the update characteristic may be further modified based on a confidence associated with the physiological signal. For example, any of the weights, the amounts of change, or the reduction factors described above with respect to Eqs. (3)-(12) may be modified based on a noise metric associated with the physiological signal or a detected stable amount of time associated with the instantaneous value indicative of fluid responsiveness.

At step 610, the processing equipment may determine a parameter indicative of fluid responsiveness of the subject based on the update characteristic selected in step 608 and a previous value indicative of fluid responsiveness. The processing equipment may determine the instantaneous value indicative of fluid responsiveness in accordance with any of the above-described methods using any of equations (1)-(12). For example, if the update characteristic is a weight associated with the instantaneous value indicative of fluid responsiveness, processing equipment may use Eq. (3) to determine the parameter indicative of fluid responsiveness based on the weight selected at step 608, the instantaneous value indicative of fluid responsiveness determined at step 604, and the previously reported value indicative of fluid responsiveness. If the update characteristic is an amount of change determined using any of Eqs. (5)-(9) as discussed above, processing equipment may use Eq. (4) to determine the parameter indicative of fluid responsiveness based on the amount of change selected at step 608 and the previous reported value indicative of fluid responsiveness. If the update characteristic is a reduction factor determined using Eqs. (11)-(12) above, processing equipment may use Eq. (10) to determine the parameter indicative of fluid responsiveness based on the reduction factor selected at step 608 the instantaneous value indicative of fluid responsiveness determined at step 604, and the previous reported value indicative of fluid responsiveness.

Figure 7:
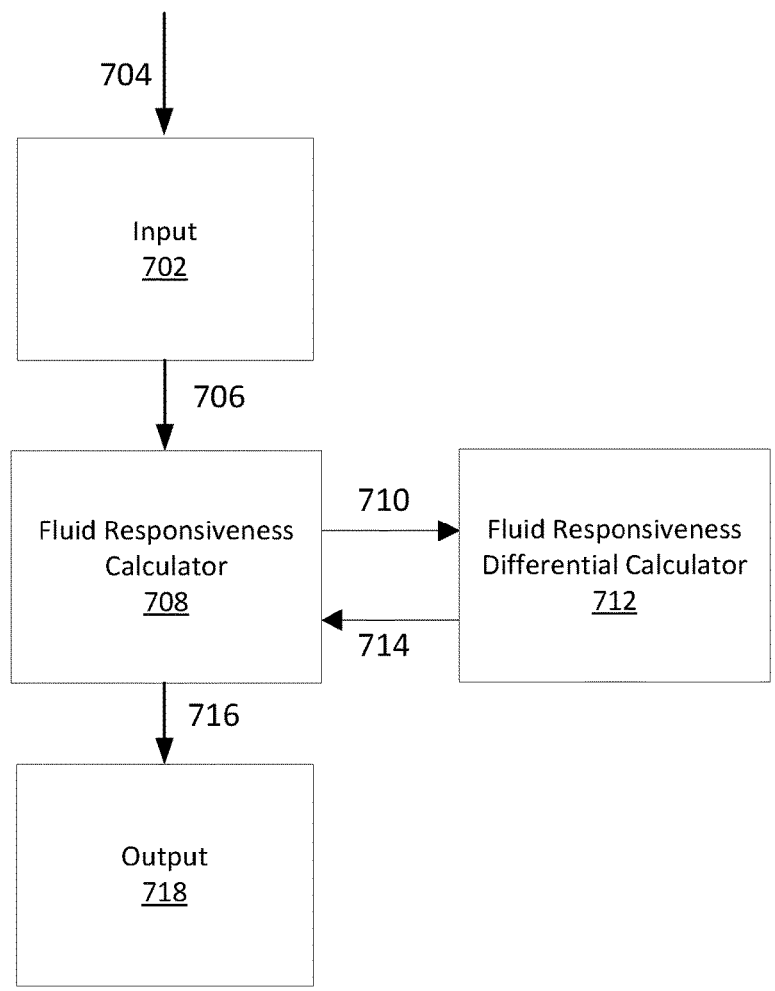
FIG. 7 shows an illustrative physiological monitor for determining fluid responsiveness in accordance with some embodiments of the present disclosure.

FIG. 7 shows an illustrative physiological monitor 700 for determining fluid responsiveness in accordance with some embodiments of the present disclosure. Monitor 700 includes input 702. In some embodiments, input 702 may include any suitable combination of components of monitor 100 for receiving a signal as described above with respect to FIG. 1. For example, input 702 may include sensor 102, light drive circuit 120, control circuit 110, and front end processing circuit 150 as described above with respect to FIG. 1, and may be configured to receive, generate and process signals as described above. In some embodiments, input 702 may include fewer components or additional components. Input 702 receives one or more physiological signals collectively referred to herein as signal 704. In some embodiments, signal 704 may include signals indicative of light absorbed by a subject. For example, signal 704 may include signals generated by an oximeter as described above with respect to FIGS. 1-2.

Input 702 generates output 706. Output 706 may include any or all of signal 704, components thereof, processed versions thereof, or any suitable combination thereof. In some embodiments, output 706 is passed to fluid responsiveness calculator 708. Fluid responsiveness calculator 708 is coupled to input 702 and may be configured to determine an instantaneous value indicative of fluid responsiveness of a subject based on the physiological signal as described above with respect to FIG. 3 and step 604 of FIG. 6. Fluid responsiveness calculator 708 may also be configured to determine a parameter indicative of fluid responsiveness based on the instantaneous value indicative of fluid responsiveness. For example, the instantaneous value indicative of fluid responsiveness may be calculated by determining DPOP for one or more of the plurality of physiological signals using Eqs. (1)-(2) and the parameter indicative of fluid responsiveness may be determined by taking an average of a series of calculated instantaneous values as described above. In some embodiments, fluid responsiveness calculator 708 may include any suitable combination of components of monitor 100 as described with respect to FIG. 1 for analyzing and processing a physiological signal. For example, fluid responsiveness calculator 708 may include front end processing circuit 150, back end processing circuit 170, any components thereof, and/or any suitable combination thereof as described above with respect to FIG. 1, and may be configured to receive signals and process them as described above. In some embodiments, fluid responsiveness calculator 708 may include fewer components or additional components. Fluid responsiveness calculator 708 generates output 710 that is passed to fluid responsiveness differential calculator 712. Output 710 may include the instantaneous value indicative of fluid responsiveness and a previous value indicative of fluid responsiveness. For example, the previous value indicative of fluid responsiveness may be a previous instantaneous value indicative of fluid responsiveness, an average of one or more previous instantaneous values indicative of fluid responsiveness, or a previously reported value indicative of fluid responsiveness.

Fluid responsiveness differential calculator 712 may determine a difference between the instantaneous value indicative of fluid responsiveness and a previous value indicative of fluid responsiveness. In some embodiments, fluid responsiveness differential calculator 712 may determine a difference between the instantaneous value indicative of fluid responsiveness and a previous value indicative of fluid responsiveness as described above with respect to step 606 of flow diagram 600. For example, fluid responsiveness differential calculator 712 may compare the instantaneous value indicative of fluid responsiveness to a previously reported value indicative of fluid responsiveness, or may subtract a previously reported value of indicative of fluid responsiveness from the instantaneous value indicative of fluid responsiveness to determine the difference. In some embodiments, fluid responsiveness differential calculator 712 may compare the difference to a threshold. Fluid responsiveness differential calculator 712 may include any suitable combination of components of monitor 100 as described with respect to FIG. 1 for analyzing and processing a physiological signal. For example, fluid responsiveness differential calculator 712 may include back end processing circuit 170, any components thereof, and/or any suitable combination thereof as described above with respect to FIG. 1, and may be configured to receive calculated values and process them as described above. In some embodiments, fluid responsiveness differential calculator 712 may include fewer components or additional components. Fluid responsiveness differential calculator 712 generates output 714 that is passed to fluid responsiveness calculator 708. Output 714 may include the difference between the instantaneous value indicative of fluid responsiveness and a previous value indicative of fluid responsiveness.

Fluid responsiveness calculator 708 may process output 714 in accordance with any of the techniques described above and generate an output 716. For example, fluid responsiveness calculator 708 may select an update characteristic based on whether output 714 indicates that fluid responsiveness of the subject is increasing or decreasing as described above with respect to step 608 of flow diagram 600 and determine a parameter indicative of fluid responsiveness based on the selected update characteristic and a previous value indicative of fluid responsiveness (e.g., the previously reported value) as described above with respect to step 610 of flow diagram 600. For example, fluid responsiveness calculator 708 may select the weight to be given to each of the instantaneous value indicative of fluid responsiveness and the previous parameter indicative of fluid responsiveness based on the output received from fluid responsiveness differential calculator 712, and may determine the updated parameter indicative of fluid responsiveness according to Eq. (3) as described above. As another example, fluid responsiveness calculator 708 may select an amount of change according to Eqs. (5)-(7) based on the output received from fluid responsiveness differential calculator 712, and may determine the updated parameter indicative of fluid responsiveness according to Eq. (4) as described above. As another example, fluid responsiveness calculator 708 may select an amount of change according to according to Eqs. (8)-(9) based on the output received from fluid responsiveness differential calculator 712 and a threshold, and may determine the updated parameter indicative of fluid responsiveness according to Eq. (4) as described above. As another example, fluid responsiveness calculator 708 may select a reduction factor of the amount of change according to Eqs. (11)-(12) based on the output received from fluid responsiveness differential calculator 712 and a threshold, and may determine the updated parameter indicative of fluid responsiveness according to Eq. (10) as described above. In some embodiments, output 716 may include instantaneous values indicative of fluid responsiveness and updated parameters indicative of fluid responsiveness. In some embodiments, output 716 may be passed to an output 718. Output 718 may include display 184 and/or communication interface 190 of monitor 104 as described above with respect to FIG. 1, any other suitable output, or any other suitable combination thereof. For example, the updated parameter indicative of fluid responsiveness may be output to be displayed on display 184, or may be output to another device via communication interface 190, so that a clinician may diagnose a subject's condition and provide treatment in response thereto.

It will be understood that while the embodiments of the present disclosure are described in terms of certain physiological signals used to calculate fluid responsiveness, the principles of this disclosure may be applied to other physiological signals and parameters. For example, the above-described embodiments may be adapted to be used with other physiological signals that experience noise that affects the determination of physiological parameters in an asymmetrical way (e.g., where noise is more likely to cause increasing values of the physiological parameter than decreasing values of the physiological parameters).

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed:
1. A physiological monitoring system comprising:
a sensor configured to:
detect light absorbed through tissue of a subject, and
generate a physiological signal based on the detected light; and
a processor coupled to the sensor configured to:
receive the physiological signal,
determine an instantaneous value indicative of fluid responsiveness of the subject based on the physiological signal,
determine a difference between the instantaneous value indicative of fluid responsiveness and a previous value indicative of fluid responsiveness of the subject,
select an update characteristic based on the difference, wherein a first update characteristic is selected based on the difference being indicative of increasing fluid responsiveness of the subject and a second update characteristic is selected based on the difference being indicative of decreasing fluid responsiveness of the subject, wherein the first update characteristic is different than the second update characteristic, and
determine a parameter indicative of fluid responsiveness of the subject based on the selected update characteristic and a previously reported value indicative of fluid responsiveness.

2. The physiological monitoring system of claim 1, wherein determining the instantaneous value indicative of fluid responsiveness comprises determining a maximum amplitude and a minimum amplitude of the physiological signal during a period.

3. The physiological monitoring system of claim 1, wherein the first update characteristic is smaller than the second update characteristic.

4. The physiological monitoring system of claim 1, wherein the processor is further configured to select the update characteristic based on an amount of difference between the instantaneous value indicative of fluid responsiveness and the previous value indicative of fluid responsiveness.

5. The physiological monitoring system of claim 1, wherein the update characteristic comprises a filter weight applied to the instantaneous value indicative of fluid responsiveness.

6. The physiological monitoring system of claim 5, wherein the filter weight is selected as one of a set of constant weights based on whether the difference is positive or negative.

7. The physiological monitoring system of claim 6, wherein the selected constant weight is smaller when the difference indicates the fluid responsiveness of the subject is increasing.

8. The physiological monitoring system of claim 5, wherein the filter weight is selected by evaluating a function based on the difference between the instantaneous value indicative of fluid responsiveness and the previous value indicative of fluid responsiveness.

9. The physiological monitoring system of claim 1, wherein the update characteristic comprises an amount of change added to the previously reported value indicative of fluid responsiveness.

10. The physiological monitoring system of claim 9, wherein the difference comprises an amount of difference and wherein the amount of change is selected by selecting one of a set of constant amounts of change based on the amount of difference.

11. The physiological monitoring system of claim 10, wherein the selected constant amount is smaller when the difference indicates the fluid responsiveness of the subject is increasing.

12. The physiological monitoring system of claim 9, wherein the difference comprises an amount of difference, and wherein the amount of change is selected by selecting one of a set of amount of change functions based on a comparison between the amount of difference and a threshold value indicative of noise.

13. The physiological monitoring system of claim 12, wherein:
the amount of change function selected when the amount of difference is greater than the threshold comprises:
determining an amount of excess over the threshold by subtracting the threshold from the amount of difference, and
multiplying the amount of excess by a constant value less than 1; and
the amount of change function selected when the amount of difference is less than or equal to the threshold consists of the amount of difference.

14. The physiological monitoring system of claim 1, wherein the update characteristic comprises a reduction factor applied to an amount of change.

15. The physiological monitoring system of claim 14, wherein the difference comprises an amount of difference, and wherein the reduction factor is selected by selecting one of a set of constant reduction factors based on a comparison between the amount of difference and a threshold.

16. The physiological monitoring system of claim 15, wherein the selected constant reduction factor is smaller when the amount of difference is greater than the threshold.

17. The physiological monitoring system of claim 1, wherein the previous value indicative of fluid responsiveness is at least one of a previous instantaneous value indicative of fluid responsiveness, an average of a plurality of previous instantaneous values indicative of fluid responsiveness, and the previously reported value indicative of fluid responsiveness.

18. A method of determining fluid responsiveness of a subject, the method comprising:
- receiving a physiological signal indicative of light attenuated by the subject;
- determining, using a processor, an instantaneous value indicative of fluid responsiveness of the subject based on the physiological signal;
- determining, using the processor, a difference between the instantaneous value indicative of fluid responsiveness and a previous value indicative of fluid responsiveness of the subject;
- selecting, using the processor, an update characteristic based on whether the difference indicates the fluid responsiveness of the subject is increasing or decreasing, wherein a first update characteristic is selected based on the difference being indicative of increasing fluid responsiveness and a second update characteristic is selected based on the difference being indicative of decreasing fluid responsiveness, and wherein the first update characteristic is different than the second update characteristic; and
- determining, using the processor, a parameter indicative of fluid responsiveness of the subject based on the selected update characteristic and a previously reported value indicative of fluid responsiveness.

19. The method of claim 18, wherein the update characteristic comprises a filter weight applied to the instantaneous value indicative of fluid responsiveness.

20. The physiological monitoring system of claim 18, wherein the update characteristic comprises an amount of change added to the previously reported value indicative of fluid responsiveness.

21. A physiological monitoring system comprising:
- an input configured to receive a physiological signal, wherein the physiological signal is indicative of light absorbed by a subject;
- a fluid responsiveness calculator coupled to the input configured to determine an instantaneous value indicative of fluid responsiveness of the subject based on the physiological signal; and
- a fluid responsiveness differential calculator coupled to the fluid responsiveness calculator configured to determine a difference between the instantaneous value indicative of fluid responsiveness and a previous value indicative of fluid responsiveness of the subject;
- wherein the fluid responsiveness calculator is further configured to:
- select a filter weight for the instantaneous value indicative of fluid responsiveness based on whether the difference indicates the fluid responsiveness of the subject is increasing or decreasing, wherein the selected filter weight is a first filter weight that is smaller when the difference indicates the fluid responsiveness of the subject is increasing than a second filter weight when the difference indicates that the fluid responsiveness of the subject is decreasing, and
- determine a parameter indicative of fluid responsiveness of the subject based on the selected filter weight, the instantaneous value indicative of fluid responsiveness, and one or more previous values indicative of fluid responsiveness.

* * * * *